United States Patent [19]

Gould et al.

[11] Patent Number: 5,273,742

[45] Date of Patent: Dec. 28, 1993

[54] BIOMEDICAL WATER SOLUBLE HYDROPHILIC POLYURETHANE POLYMERS AND METHOD OF USE THEREOF

[75] Inventors: Francis E. Gould; Murray H. Reich, both of Princeton, N.J.

[73] Assignee: Tyndale Plains-Hunter Ltd., Princeton, N.J.

[21] Appl. No.: 814,754

[22] Filed: Dec. 30, 1991

[51] Int. Cl.$^5$ .................... A61K 31/74; A61K 9/00
[52] U.S. Cl. .................... 424/78.08; 424/78.04; 424/78.05; 424/422; 424/423; 424/427; 514/912; 514/913; 514/914; 514/915; 514/825
[58] Field of Search .............. 514/912, 913, 914, 915, 514/825; 424/78.04, 78.05, 78.08, 422, 423, 427

[56] References Cited

U.S. PATENT DOCUMENTS

| | | |
|---|---|---|
| 3,767,788 | 10/1973 | Rankin .................... 424/78.04 |
| 3,822,238 | 7/1974 | Blair et al. . |
| 3,975,350 | 8/1976 | Hudgin et al. . |
| 4,156,066 | 5/1979 | Gould . |
| 4,156,067 | 5/1979 | Gould . |
| 4,255,550 | 3/1981 | Gould . |
| 4,359,558 | 11/1982 | Gould et al. . |
| 4,408,023 | 10/1983 | Gould et al. . |
| 4,424,305 | 1/1984 | Gould et al. . |
| 4,439,583 | 3/1984 | Gould et al. . |
| 4,439,584 | 3/1984 | Gould et al. . |
| 4,439,585 | 3/1984 | Gould et al. . |
| 4,451,635 | 5/1984 | Gould et al. . |
| 4,454,309 | 6/1984 | Gould et al. . |
| 4,490,423 | 12/1984 | Gould et al. . |
| 4,496,535 | 1/1985 | Gould et al. . |
| 4,704,130 | 11/1987 | Gilding et al. .................... 521/50 |
| 4,729,914 | 3/1988 | Kliment et al. . |
| 4,743,673 | 5/1988 | Johnston et al. . |
| 4,780,512 | 10/1988 | Gould et al. . |
| 4,789,720 | 12/1988 | Teffenhart . |
| 4,798,876 | 1/1989 | Gould et al. . |
| 4,810,543 | 3/1989 | Gould et al. . |
| 4,810,582 | 3/1989 | Gould et al. . |
| 4,830,860 | 5/1989 | Ranade .................... 424/427 |
| 4,865,846 | 9/1989 | Kaufman .................... 424/427 |
| 4,920,172 | 4/1990 | Daoud et al. . |
| 5,000,955 | 3/1991 | Gould et al. . |

*Primary Examiner*—Peter F. Kulkosky
*Attorney, Agent, or Firm*—Mathews, Woodbridge & Collins

[57] ABSTRACT

A method for treating a body condition comprising introducing an aqueous solution of a water soluble polyether polyurethane into said body condition.

2 Claims, No Drawings

BIOMEDICAL WATER SOLUBLE HYDROPHILIC POLYURETHANE POLYMERS AND METHOD OF USE THEREOF

FIELD OF THE INVENTION

The claimed invention relates to polyurethane polymers specifically adapted to methods of using such polyurethane polymers as a replacement for body fluids.

BACKGROUND OF THE INVENTION

Presently, sodium hyaluronate, a naturally occurring material, is used as a replacement fluid for eyes and joints.

Water soluble polyurethane polymers having varying amounts of water have been known for use as microcapsules for drug delivery, culture media, cosmetics and the like.

U.S. Pat. No. 5,000,955—Gould et al., of common ownership and partial common inventorship herewith—discloses thermally reversible hydrogels made from polyurethane polymers, comprising water and a gel forming hydrophilic polyurethane polymer, made by adding an alkylene diisocyanate with a glycol component comprising polyoxyethylene glycols in a mole weight ratio of NCO/OH from 0.9/1 to about 0.98/1. The reaction mixture is anhydrous. To obtain dry materials, the reactants are subjected to heat, vacuum or a desiccating agent. The glycols are dried since they often contain sufficient water which may alter the properties of the gel.

U.S. Pat. No. 4,810,582—Gould et al., of common ownership and partial common inventorship herewith—discloses NCO/OH ratios of 0.5/1 to 0.9/1 and water levels of 0.1% to 0.5% for use in water insoluble hydrophilic polyurethane polymers.

U.S. Pat. No. 4,810,582 teaches the use of hydrophilic polyurethane hydrogels to encapsulate active agents, wherein the active agent is leached from the water swellable, water insoluble and water soluble polyurethane polymers. The hydrogels are useful as nontoxic culture media, gel matrices, and bacterial cells, and function as nontoxic media for electrophoretic separation of biological substances. The hydrogels are useful in cosmetic applications, as in the preparation of face masks, for example.

BRIEF DESCRIPTION OF THE INVENTION

The claimed invention is drawn to a method for treating a body condition comprising introducing an aqueous solution of a water soluble polyurethane polymer into said body condition.

The polyurethane polymer solution may be removed upon elimination of said body condition.

Preferably, the claimed invention is directed to the methods of replacing ocular fluid and intra-articular fluid by introducing a water soluble polyether polyurethane into the eye and joint respectively.

DESCRIPTION OF THE INVENTION

It is an object of this invention to provide a method of using a water soluble polyurethane polymer in the human body as a supplement or replacement for natural body fluids. The polyurethane polymer protects, lubricates, supplements, expands and replaces body fluids. The polymer may be used in a method of treating a disease or condition and protecting a particular body site including, but not limited to, eyes and body sites such as joints, for example. Thus, the composition may be used in a method of replacing intraocular fluid, including replacing natural tears, as well as in a method for replacing intra-articular fluid. As used herein, replacing includes supplementing and expanding body fluids.

The composition of the present invention may also be useful in methods of expanding blood, replacing fluid in breast implants, replacing or supplementing synovial, spinal, cerebrospinal, interstitial, labyrinthine, subarachnoid, amniotic, allantoic, peritoneal and Scarpas's fluid and the like. In addition, the polymer solutions may be used during surgery to bathe the body site undergoing surgical manipulation. The methods set forth above are carried out in any conventional manner of replacing body fluids available to one of ordinary skill in the art.

The duration of treatment varies with the body condition. The method of treating may be indefinite, such that the fluid in a certain body site is replaced in the method of the claimed invention, such as in a method of replacing intra-articular fluid to bathe a joint. Body fluids may also be supplemented or expanded, blood and natural tears for example, may be expanded by the method of the claimed invention. Also, where a body condition is temporary, the method may be used to deliver replacement body fluid until elimination of the body condition. The polyurethane polymer is then removed from the affected body site or naturally replaced with the natural body fluid.

Polymers useful in the present invention are nontoxic, non-inflammatory, water soluble, thermally reversible and viscoelastic. The reversibility and viscoelasticity of the polyurethane polymers permits the flow of polymer solutions in a method of delivering polymer solutions to the body. Properties which are a result of the thermally reversible nature of polymers used in accordance with the present invention, including but not limited to plasticity and fluidity, adapt the polymer solution to flow under pressure.

In addition, the viscoelastic properties can be adapted to the particular specific application by modifying the molecular weight of the diol component and the polymer, water portion of the diol, NCO/OH ratio, and concentration of polymer in the solvent. The viscoelastic properties permits the polymer solution to be sensitive to pressure, becoming less viscous as the shear rate increases. The degree of viscoelasticity can be modified by changing the reaction formula variables and the concentration of polymer in the solution.

Additional unique physical properties of the polyether polyurethane hydrogels useful in this invention include lubricity and slip properties. Further, these hydrogels are nontoxic, tissue compatible, non-inflammatory, possess optical clarity, transport oxygen, and do not scar tissue.

The water soluble hydrophilic polyurethanes comprise the reaction product of an alkylene diisocyanate, a known amount of water, and a glycol component comprising one or more polyoxyethylene glycols, optionally mixed with one or more lower molecular weight ethylene glycols. The total glycol component has a number average molecular weight from about 1,000 to about 20,000 and wherein the amount by weight of the diisocyanate in the reaction is from about 5% to about 25%, and wherein the amount of water is from 0.01% to 10% and wherein the reaction product is mixed in an aqueous medium.

The mole weight ratio of NCO/OH, as a result of the diisocyanate to the hydroxyl-containing compounds, varies depending on the use of the polyurethane polymer. The NCO to OH ratio for intraocular fluids is 0.50 to 1.2, preferably 0.65 to 1.2, more preferably 0.75 to 1.2 and most preferably 0.80–1.2; tears and intra-articular fluids have NCO/OH ratios of 0.1 to 1.0, preferably 0.2 to 0.90, more preferable from 0.3 to 0.85 and most preferably from 0.35 to 0.80. Thus, the NCO to OH ratio varies from about 0.1 to 1.0 to about 0.8 to 1.2.

The water in the reaction may range from 0.001% to 10%, preferably from 0.01% to 5%, more preferably from 0.02% to 3% and most preferably from 0.03% to 2.0% based upon the weight of reacting materials.

An important aspect of the current invention is the temperature at which the catalyst is added, termed herein as the starting temperature, to control the viscosity of the hydrophilic polyurethane.

The starting temperature of the reaction may vary from 30° to 120° C., preferably from 40° to 100° C., and more preferably from 50° to 90° C.

In addition to methylenebis(cyclohexyl-4-4'-isocyanate) other diisocyanates can be used in preparing suitable hydrophilic polyurethane polymers. These other diisocyanates include both aliphatic and aromatic types although the aliphatics are preferred. Representative examples of the preferred aliphatic diisocyanates include, but are not limited to tetramethylene diisocyanate, hexamethylene diisocyanate, trimethylene diisocyanate, trimethylhexamethylene diisocyanate, cyclohexyl 1,2 diisocyanate, cyclohexylene 1,4 diisocyanate, and aromatic diisocyanates such as 2,4-toluene diisocyanates and 2,6-toluene diisocyanates. Also suitable are the isocyanate equivalents which form urethane linkages as exemplified by nitrile carbonates, such as adiponitrile carbonate of the formula (see U.S. Pat. No. 4,810,543, of common ownership and partial common inventorship herewith).

Alkylene glycols and polyoxyalkylene glycols may be purchased for chemical supply houses. Typical commercial products are the polyoxyethylene glycols made by Union Carbide Corporation under the trademark Carbowax ®, of which Carbowax ® 1450, Carbowax ® 4500, Carbowax ® 8000 and Carbowax ® 20,000 are examples (Carbowax ® is identified by average molecular weight).

The polymers of this invention are hydrophilic, have unique and valuable rheological, lubricating and slip properties, compatible with body fluids, and also serve as a transfer and carrier medium through which molecules can move. The polymer solutions are readily injected through a small needle, a 27 gauge needle for example, to an affected body site. Alternatively, the polymer solutions may be delivered via a dropper, into the eye for example.

It is an object of this invention to provide polymers having a wide range of viscosities when placed in solution. When in place in the body site, the polymer may become viscous and take on the characteristics of the natural body fluid to provide cushioning or shock absorption for the body part which the polymer bathes. For example, the polymer solution may be adapted to become viscous upon attaining body temperature in a method of replacing or supplementing eye or joint fluid. Thus, the polymer may be added at one temperature and become viscous as it adapts to the environment of the joint, eye or other body site. The polymer may be readily washed out, with water, saline and other physiologic solutions for example, after its presence is no longer necessary.

The intra-articular method of using the polymer solution assists in the correction of rheumatologic problems such as damage, lameness, inflammation and swelling, and the like, for example. The polymer solution may be used in a method of articulating joints such as knees, shoulders, elbows, feet, hips, and wrists.

The polymer of the claimed invention may be used during intraocular surgery and as artificial tears. The polymer solution does not cause the development of cataracts, and does not affect intraocular pressure postoperatively. The polymer also does not block the drainage system of the aqueous humor through the chamber angle.

Accordingly, the method of the claimed invention is drawn to treating a body condition comprising introducing an aqueous solution of a water soluble polyether polyurethane into the body condition. The polyether polyurethane solution may be removed upon elimination of the body condition.

Specifically, the present invention is directed to a method for replacing ocular fluid in a mammalian eye by introducing an aqueous solution of a water soluble polyether polyurethane into the eye.

Further, a method for replacing intra-articular fluid in a mammalian joint by introducing an aqueous solution of a water soluble polyether polyurethane into the joint is an embodiment of the claimed invention.

EXAMPLE 1

A polyether polyurethane was prepared by mixing 30.7 parts of Carbowax ® 1450 polyoxyethylene glycol (Union carbide Corporation), 99.3 parts of Carbowax ® 8000 polyoxyethylene glycol (Union Carbide Corporation) and 3.84 parts of diethylene glycol with stirring at 70° C. to form an homogeneous melt. While continuing to stir, 18.4 parts of Desmodur W ® diisocyanate (also known as methylenebis(cyclo-hexyl-4-isocyanate), Mobay Chemical Corp.) was added. To this mixture, a stannous catalyst was added and the mixture was allowed to exotherm. The reaction mass was then poured into a polypropylene pan, and the pan was placed in a circulating oven at 100° C. for one hour to cure the polymer.

After cooling to ambient room temperature, the polymer mass was cut into small pieces which are mixed with water to form a mixture containing 4.0% solids. The mixture was mixed on a roller mill for 24 hours. The swollen polymer was heated at 60° C. and then cooled to room temperature. The heating, cooling, and mixing cycle was repeated several times.

In an intraocular surgical procedure, a conjunctival flap was prepared on anesthetized animals, and the anterior chamber was emptied. The hydrogel of Example 1 was injected through a syringe and left in the eye for one to two minutes. A 10 mm perforating incision was made at the sclerocorneal junction, and the antechamber was rinsed with 5 ml of a balanced salt solution. The wound was closed with a 10-0 nylon suture.

Postoperatively, based on measurements of corneal thickness and intraocular pressure and observations of inflammation, there were no significant changes in eyes inoculated with solution Example 1 compared to the usual 1% sodium hyaluronate. The corneal thickness increased while staying transparent in all cases. Cataracts did not develop. The polymer solution was readily washed out of the eye. Also, it did not block the drainage system of the aqueous humor through the chamber angle.

Histopathological examinations of the anterior segment showed no adverse reactions to the use of Example 1 solution. Example 1 solution maintained the anterior chamber as well as 1% sodium hyaluronate. It was essentially nontoxic by standard histopathology.

Solutions of any desired solids content and of different aqueous consistency may be prepared by mixing the required amount of dry polymer with water, and heating the mixture to about 60° C. with stirring. Solutions can be made containing 0.5 to 7% of the polymers described herein.

EXAMPLE 2

A polyether polyurethane was prepared by mixing 99.3 parts of Carbowax ® 8000 polyoxyethylene glycol (Union Carbide Corporation), 30.7 parts of Carbowax ® 1450 polyoxyethylene glycol (Union Carbide Corporation), and 3.8 parts of diethylene glycol with stirring at 70° C. to form an homogeneous melt. While continuing the stirring, 18.4 parts of Desmodur W ® diisocyanate (methylenebis(cyclohexyl-4-isocyanate), Mobay Chemical Corp.) was added. When the temperature reached 70° C., 15 cc of $T_9$ catalyst (stannous octoate, Air Products and Chemicals, Inc.) was added and the mixture was allowed to exotherm to 75° C. The reaction mass was then poured into a polypropylene pan, and the pan was placed in a circulating oven at 100° C. for one hour to cure the polymer.

After cooling to ambient room temperature, the polymer mass was cut into small pieces which were mixed with water to form a mixture containing 5% solids. The mixture was mixed on a roller mill for 24 hours. The swollen polymer was heated at about 65° C. and for about one hour and then cooled to room temperature. The heating, cooling and mixing cycle was repeated several times. The polymer solution had a viscosity of 453 cps.

Using a 27 gauge needle, 5 cc of 3% solution of this hydrogel may be injected directly into the joint space of the elbow of the left foreleg of a rabbit. Repeated intra-articular injections can provide relief of arthritic symptoms.

EXAMPLE 3

A polyether polyurethane was prepared by mixing 805 parts of Carbowax ® 8000 polyoxyethylene glycol (Union Carbide Corporation), 22.5 parts of diethylene glycol with stirring at 70° C. to form an homogeneous melt. The glycols were dried to 0.0845% water. Sufficient water was added, 2.73 parts to bring the water content in the batch to 0.3%. While stirring, 80.8 parts of Desmodur W ® diisocyanate (methylenebis(cyclohexyl-4-isocyanate), Mobay Chemical Corp.) was added to provide an NCO/OH value of 0.59. When the temperature reached 62° C., 0.75 cc of $T_{12}$ catalyst (dibutyl tin dilaurate, Air Products and Chemicals, Inc.) was added and the mixture was allowed to exotherm to 68° C. The reaction mass was then poured into a polypropylene pan, and the pan was placed in a circulating oven at 100° C. for one hour to cure the polymer.

After cooling to ambient room temperature, the polymer mass was cut into small pieces which were mixed with water to form a mixture containing 5% solids. The mixture was mixed on a roller mill for 24 hours. The swollen polymer was heated at about 65° C. and for about one hour and then cooled to room temperature. The heating, cooling and mixing cycle was repeated several times. The polymer solution had a viscosity of 14 cps.

Using a 27 gauge needle, 6 cc of 3% solution of this hydrogel may be injected directly into the joint space of the elbow of the left foreleg of a rabbit. The injection provided relief of arthritic symptoms.

EXAMPLE 4

A polyether polyurethane was prepared by mixing 592.1 parts of Carbowax ® 8000 polyoxyethylene glycol (Union Carbide Corporation), 183 parts of Carbowax ® 1450 polyoxyethylene glycol (Union Carbide Corporation), 7.984 parts of water, and 22.93 parts of diethylene glycol with stirring at 60° C. to form a homogeneous melt. While continuing the stirring, 109.91 parts of Desmodur W ® diisocyanate (methylenebis(cyclohexyl-4-isocyanate), Mobay Chemical Corp.) was added to produce an NCO/OH ratio of 0.31. When the temperature reached 64° C., 0.75 cc of $T_9$ catalyst (stannous octoate, Air Products and Chemicals, Inc.) was added and the mixture exothermed to 65° C., in a circulating oven at 100° C. for one hour to cure the polymer.

After cooling to ambient room temperature, the polymer mass was cut into small pieces which were mixed with water to form a mixture containing 5% solids. The mixture was mixed on a roller mill for 24 hours. The swollen polymer was heated at about 65° C. and for about one hour and then cooled to room temperature. The heating, cooling and mixing cycle was repeated several times. The polymer solution had a viscosity of 14 cps.

Using an eye dropper, two drops of a 3% aqueous solution may be dropped into the eye for use as artificial tears and to relieve the sensation of dry eyes. Also, using a 27 gauge needle, 5 cc of 5% aqueous solution of this hydrogel may be injected directly into the joint of an arthritic elbow of a rabbit.

The claimed invention may be used in a method of replacing natural tears, expanding blood and replacing fluid in breast implants. The claimed invention may also be used in methods of replacing or supplementing intra-ocular, intra-articular, synovial, spinal, cerebrospinal, interstitial, labyrinthine, subarachnoid, amniotic, allantoic, peritoneal and Scarpas's fluid, and to bathe a body site undergoing surgical manipulation, and the like.

While this invention has been disclosed with reference to a specific embodiment, it is apparent that other embodiments and equivalent variations of this invention may be devised by those skilled in the art without departing from the true spirit and scope of this invention. The appended claims are intended to be construed to include all such embodiments and equivalent variations.

What is claimed is:

1. A method for replacing ocular fluid in a mammalian eye by introducing an aqueous solution of a water soluble hydrogel forming polyether polyurethane in an amount of 0.5 to 7.0% weight of said polymer percent, said polyether polyurethane is prepared by reacting at a NCO/OH ratio of from about 0.8 to about 1.2, said polyether polyurethane is prepared by mixing a diisocyanate with a glycol component comprising one or more polyoxyethylene glycols, optionally mixed with one or more lower molecular weight ethylene glycols the total glycol component having an average molecular weight of from about 1,000 to about 20,000 and mixing the reaction product in an aqueous medium wherein there are no adverse effects to eyes so treated.

2. A method for replacing intra-articular fluid in a mammalian joint by directly introducing into said joint an aqueous solution of a water soluble hydrogel forming polyether polyurethane in an amount of 0.5 to 7.0% weight percent of said polymer said polyether polyurethane is prepared by reacting at a NCO/OH ratio of from about 0.3 to about 0.85, said polyether polyurethane is prepared by mixing a diisocyanate with a glycol component comprising one or more polyoxyethylene glycols, optionally mixed with one or more lower molecular weight ethylene glycols the total glycol component having an average molecular weight of from about 1,000 to about 20,000 and mixing the reaction product in an aqueous medium wherein relief of arthritic symptoms is provided.

* * * * *